(12) United States Patent
Kitayama

(10) Patent No.: US 9,018,374 B2
(45) Date of Patent: Apr. 28, 2015

(54) CRYSTAL OF AMIDE COMPOUND

(75) Inventor: Masato Kitayama, Osaka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 173 days.

(21) Appl. No.: 13/704,039

(22) PCT Filed: Jun. 15, 2011

(86) PCT No.: PCT/JP2011/063735
§ 371 (c)(1),
(2), (4) Date: Dec. 13, 2012

(87) PCT Pub. No.: WO2011/158880
PCT Pub. Date: Dec. 22, 2011

(65) Prior Publication Data

US 2013/0090337 A1 Apr. 11, 2013
US 2013/0252954 A2 Sep. 26, 2013

(30) Foreign Application Priority Data

Jun. 16, 2010 (JP) ................. 2010-137194

(51) Int. Cl.
C07D 413/14 (2006.01)
A61K 31/5377 (2006.01)
C07D 401/12 (2006.01)

(52) U.S. Cl.
CPC .......... *C07D 413/14* (2013.01); *A61K 31/5377* (2013.01); *C07D 401/12* (2013.01)

(58) Field of Classification Search
CPC . C07D 413/14; C07D 401/12; A61K 31/5377
USPC ........................ 514/235.8; 544/130
See application file for complete search history.

(56) References Cited

U.S. PATENT DOCUMENTS

| | | | |
|---|---|---|---|
| 6,894,051 B1 | 5/2005 | Zimmermann et al. |
| 7,732,626 B2 | 6/2010 | Yasuma et al. |
| 8,088,821 B2 | 1/2012 | Yasuma et al. |
| 8,163,773 B2 | 4/2012 | Breitenstein et al. |
| 2002/0115858 A1 | 8/2002 | Zimmermann et al. |
| 2005/0004190 A1 | 1/2005 | Kawazoe et al. |
| 2005/0192284 A1 | 9/2005 | Zimmermann et al. |
| 2006/0030568 A1 | 2/2006 | Zimmermann et al. |
| 2006/0135523 A1 | 6/2006 | Cheng et al. |
| 2006/0223831 A1 | 10/2006 | Kinoyama et al. |
| 2007/0004736 A1 | 1/2007 | Kubo et al. |
| 2007/0004746 A1 | 1/2007 | Zimmermann et al. |
| 2008/0214633 A1 | 9/2008 | Kawazoe et al. |
| 2009/0208584 A1 | 8/2009 | Yoshinari et al. |
| 2009/0233920 A1 | 9/2009 | Breitenstein et al. |
| 2010/0004312 A1 | 1/2010 | Yasuma et al. |
| 2010/0137587 A1 | 6/2010 | Takanobu et al. |
| 2010/0197761 A1 | 8/2010 | Yasuma et al. |
| 2011/0009389 A1 | 1/2011 | Kubo et al. |
| 2011/0178057 A1 | 7/2011 | Kuroita et al. |
| 2012/0046338 A1 | 2/2012 | Yasuma et al. |
| 2012/0149733 A1 | 6/2012 | Cherney et al. |

FOREIGN PATENT DOCUMENTS

| | | |
|---|---|---|
| JP | 2001-510192 | 7/2001 |
| JP | 2004-331657 | 11/2004 |
| WO | 03/037881 | 5/2003 |
| WO | 2004/048363 | 6/2004 |
| WO | 2004/111033 | 12/2004 |
| WO | 2006/132440 | 12/2006 |
| WO | 2007/006534 | 1/2007 |
| WO | 2008/001931 | 1/2008 |
| WO | 2009/014217 | 1/2009 |
| WO | 2009/154300 | 12/2009 |

OTHER PUBLICATIONS

Opposition published Feb. 19, 2013 in corresponding Costa Rican Application No. 2013-0014, with English translation.
International Search Report issued Jul. 19, 2011 in International (PCT) Application No. PCT/JP2011/063735.
Mino R. Caira, "Crystalline Polymorphism of Organic Compounds", Topics in Current Chemistry, vol. 198, 1998, pp. 164-208.
Technical Examination (Office Action) issued Jun. 5, 2014 in corresponding Colombia Patent Application No. 13006575.
Examiner's Report issued Feb. 17, 2014 in the corresponding Chilean Application No. 3526-2012.
MA 34377, Jul. 3, 2013 (corresponds to Solicitud 3521-12 and corresponds to US 2012/0149733).

*Primary Examiner* — Rebecca Anderson
(74) *Attorney, Agent, or Firm* — Wenderoth, Lind & Ponack, L.L.P.

(57) ABSTRACT

Provision of crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride which has a superior rennin inhibitory activity and is useful as a prophylactic or therapeutic agent for hypertension and various organ disorders caused by hypertension, and the like. Crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride having an X-ray powder diffraction pattern showing characteristic peaks at interplanar spacings (d) of around 26.43±0.2, 7.62±0.2 and 4.32±0.2 angstroms.

7 Claims, 1 Drawing Sheet

CRYSTAL OF AMIDE COMPOUND

TECHNICAL FIELD

The present invention relates to a crystal of an amide compound which has a superior rennin inhibitory activity and is useful as a prophylactic or therapeutic agent of hypertension or various organ disorders caused by hypertension, and the like.

BACKGROUND OF THE INVENTION

Patent document 1 (WO 2009/154300) describes 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride which has a rennin inhibitory action and is useful as a prophylactic or therapeutic agent for hypertension or various organ disorders caused by hypertension, and the like.

DOCUMENT LIST

Patent document

Patent document 1: WO 2009/154300

SUMMARY OF THE INVENTION

Problems to be Solved by the Invention

There is a demand for a prophylactic or therapeutic agent for hypertension or various organ disorders caused by hypertension, which is superior in the effectiveness and safety. The present invention aims to provide a novel crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride which is useful as a prophylactic or therapeutic agent for hypertension or various organ disorders caused by hypertension.

Means of Solving the Problems

The present inventors have conducted an intensive search and succeeded in providing 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a stable crystal having low hygroscopicity and high melting point. They have found that the crystal is sufficiently satisfactory as a medicament, and completed the present invention based on these findings.

Accordingly, the present invention relates to (1) a crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride having a powder X-ray diffraction pattern showing characteristic peaks at interplanar spacings (d) of around 26.43±0.2, 7.62±0.2 and 4.32±0.2 angstroms (hereinafter sometimes to be abbreviated as the crystal of the present invention), (2) a crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride having a powder X-ray diffraction pattern showing characteristic peaks at interplanar spacings (d) of around 26.43±0.2, 7.62±0.2, 4.32±0.2, 3.08±0.2, 2.59±0.2 and 2.33±0.2 angstroms (hereinafter sometimes to be abbreviated as "type B crystal"), (3) a medicament comprising the crystal of the aforementioned (1) or (2), (4) the medicament of the aforementioned (3), which is a rennin inhibitor, (5) the medicament of the aforementioned (3), which is a prophylactic or therapeutic agent for a circulatory disease, (6) the medicament of the aforementioned (3), which is a prophylactic or therapeutic agent for hypertension and/or various organ disorders caused by hypertension, (7) the medicament of the aforementioned (3), which is a prophylactic or therapeutic agent for a renal disease, (8) a method for the prophylaxis or treatment of a circulatory disease in a mammal, comprising administering an effective amount of the crystal of the aforementioned (1) or (2) to said mammal, (9) a method for the prophylaxis or treatment of hypertension and/or various organ disorders caused by hypertension in a mammal, comprising administering an effective amount of the crystal of the aforementioned (1) or (2) to said mammal,

(10) a method for the prophylaxis or treatment of a renal disease in a mammal, comprising administering an effective amount of the crystal of the aforementioned (1) or (2) to said mammal,

(11) use of the crystal of the aforementioned (1) or (2) for the production of a prophylactic or therapeutic agent for a circulatory disease,

(12) use of the crystal of the aforementioned (1) or (2) for the production of a prophylactic or therapeutic agent for hypertension and/or various organ disorders caused by hypertension,

(13) use of the crystal of the aforementioned (1) or (2) for the production of a prophylactic or therapeutic agent for a renal disease,

(14) the crystal of the aforementioned (1) or (2) for use in the prophylaxis or treatment of a circulatory disease,

(15) the crystal of the aforementioned (1) or (2) for use in the prophylaxis or treatment of hypertension and/or various organ disorders caused by hypertension,

(16) the crystal of the aforementioned (1) or (2) for use in the prophylaxis or treatment of a renal disease, and the like.

Effect of the Invention

The crystal of the present invention (e.g., the aforementioned type B crystal) is useful as a pharmaceutical product since it has a superior rennin inhibitory action, a hypotensive action and/or an organ protecting action against various organ disorders caused by hypertension and the like, and low toxicity.

DETAILED DESCRIPTION OF THE INVENTION

Figure 1:
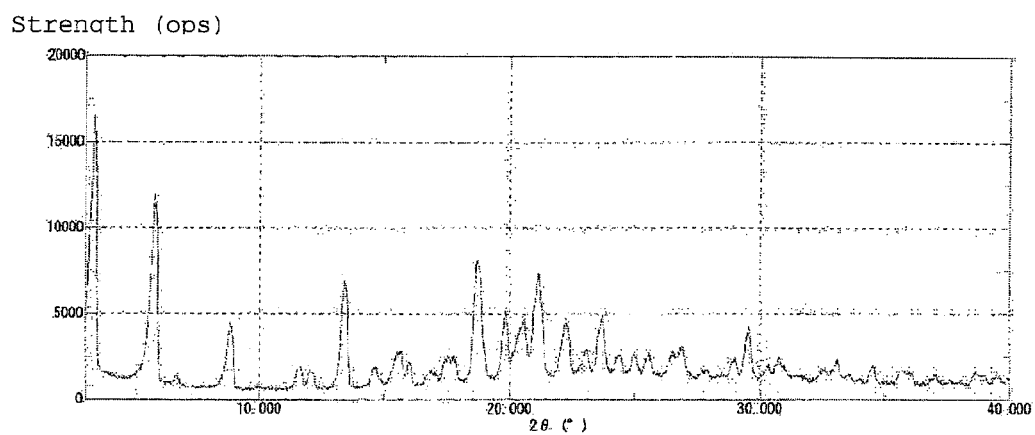
FIG. 1 shows the powder X-ray diffraction pattern of the type B crystal of Example 6.
Figure 2:
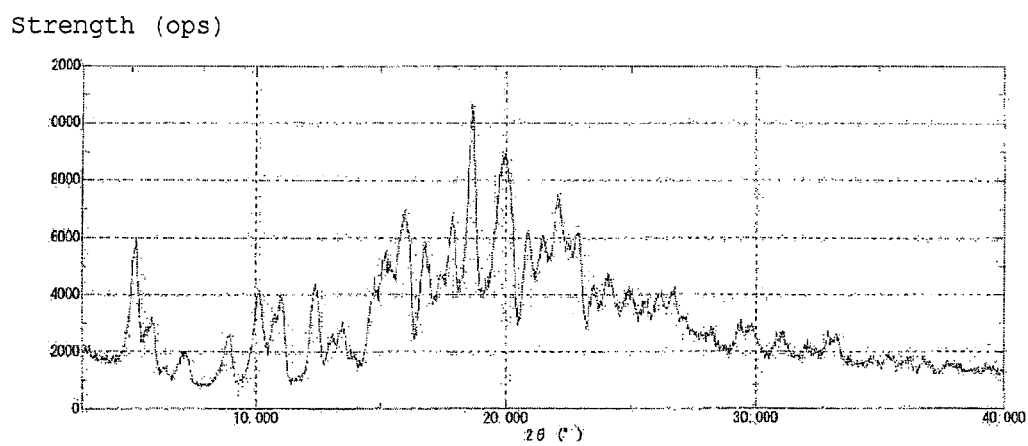
FIG. 2 shows the powder X-ray diffraction pattern of the type A crystal of Reference Example 3.

The crystal of the present invention may be a hydrate crystal, a non-hydrate crystal, a solvate crystal other than hydrate, or a non-solvate crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (hereinafter sometimes to be abbreviated as "amide compound").

Examples of the "hydrate" include 0.5 hydrate to 5 hydrate. Among these, 0.5 hydrate, 1.0 hydrate, 1.5 hydrate, 2.0 hydrate and 2.5 hydrate are preferable. Particularly preferred are 0.5 hydrate, 1.0 hydrate and 1.5 hydrate.

The crystal of the present invention may be a deuterated form.

The crystal of the present invention may be labeled with an isotope (e.g., $^3$H, $^{14}$C, $^{35}$S, $^{125}$I, etc.).

Examples of the solvate crystal of the amide compound include alcohol solvate crystals such as methanol solvate crystal, ethanol solvate crystal and the like (preferably $C_{1-6}$ alcohol solvate crystal), organic solvate hydrate crystals impregnated with water and organic solvent (e.g., alcohol solvate hydrate crystals such as methanol hydrate crystals, ethanol hydrate crystals, etc., preferably $C_{1-6}$ alcohol hydrate crystals) and the like.

The crystal of the present invention can be produced by crystal transition of an amorphous amide compound or other crystal of the amide compound. The crystal transition is a phenomenon where a crystal structure changes when the temperature or pressure exceeds a certain level.

Examples of the method of crystal transition include, methods known per se, for example, crystallization from solution (e.g., a concentration method, a slow cooling method, a reaction method (diffusion method, electrolysis method), a hydrothermal growth method, a fusing agent method), crystallization from vapor (e.g., a gasification method (sealed tube method, gas stream method), a gas phase reaction method, a chemical transportation method), crystallization from melt (e.g., a normal freezing method (pulling-up method, temperature gradient method, Bridgman method), a zone melting method (zone leveling method, float zone method), a special growth method (VLS method, liquid phase epitaxy method), a stream fog method (in which a crystal is dissolved in a solvent and, after filtration, the solvent is evaporated under atmospheric conditions), a slurry method (in which a crystal is added to a solvent such that excess solid remains therein to give a suspension, the suspension is stirred at room temperature or under heating or under cooling and the solid is collected by filtration), and methods such as drying under reduced pressure, grinding, pulverization, pressurization, and the like.

To obtain the crystal of the present invention, a slurry method is particularly preferable from among the above-mentioned methods. Particularly, a method of adding a crystal of an amide compound to a solvent such that an excess solid remains to give a suspension, stirring the suspension, and collecting the solid by filtration is preferable. Solvents to be used include, for example, aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, 2-propanol, etc.), water, and the like. These solvents may be used singly or in a mixture of two or more kinds at an appropriate ratio (e.g., 1:1 to 1:100). Preferred are alcohols (e.g., 2-propanol etc.), ketones (methyl ethyl ketone etc.) and esters (e.g., ethyl acetate etc.), and more preferred are ketones (e.g., methyl ethyl ketone etc.).

The amount of the solvent to be used is generally about 5 mL-about 65 mL, preferably about 5 mL-about 25 mL, relative to a crystal (1 g) of an amide compound.

The suspension is preferably stirred at room temperature or about 30° C.-about 60° C., more preferably at about 30° C.-about 60° C. In the present specification, the room temperature means about 15° C.-about 30° C. The time of stirring at about 30° C.-about 60° C. is generally about 30 min-about 4 hr, preferably about 2 hr-about 4 hr. The cooling temperature is room temperature. The time of stirring under cooling is generally about 30 min-about 24 hr, preferably about 30 min-about 2 hr. Crystals in a suspension can be isolated by a method known per se such as filtration and the like. The filtration temperature is room temperature, preferably about 20° C.-about 30° C.

Alternatively, the method of stirring the suspension at about 0-about 10° C. and then collecting the crystals by filtration at about 0-about 10° C. may be employed.

The crystal of the present invention can be obtained by drying the obtained crystals by a method known per se. The drying may be performed under reduced pressure or by ventilation. The drying temperature is preferably not more than about 60° C., more preferably about 45° C.-about 55° C.

Crystals other than the crystal of the present invention can be produced by, for example, the method described in WO 2009/154300 or a method analogous thereto. The crystal of the amide compound described in WO 2009/154300 is called type A crystal.

For analyzing the obtained crystal, X-ray diffraction crystallographic analysis method is commonly employed. In addition, crystal orientation can also be determined by a mechanical method, an optical method (e.g., FT-Raman spectrum, solid-state NMR spectrum etc.), and the like.

The peak of the spectrum obtained by the above-mentioned analysis method inevitably contains a certain measurement error by its nature. A crystal with a spectrum peak within the error range is also encompassed in the crystal of the present invention. For example, "±0.2" in the interplanar spacing (d) of the powder X-ray diffraction means that the error is tolerable.

Examples of the crystal of the 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride in the present invention include a crystal having a powder X-ray diffraction pattern showing characteristic peaks at interplanar spacings (d) of 26.43±0.2, 7.62±0.2 and 4.32±0.2 angstroms, preferably, a crystal having a powder X-ray diffraction pattern showing characteristic peaks at interplanar spacings (d) of 26.43±0.2, 7.62±0.2, 4.32±0.2, 3.08±0.2, 2.59±0.2 and 2.33±0.2 angstroms (type B crystal).

Thus crystal of the present invention is useful as a pharmaceutical product since it has an excellent rennin inhibitory action, a hypotensive action and the like, as well as low toxicity. Moreover, since the crystal of the present invention shows decreased hygroscopicity and is superior in the stability, it can be handled easily and can be processed into a solid pharmaceutical composition with good reproducibility.

The crystal of the present invention is useful as a medicament for suppressing the rennin-angiotensin system (RA system) since it acts as a rennin inhibitor on mammals (e.g., mouse, rat, hamster, rabbit, cat, dog, bovine, sheep, monkey, human etc.) to inhibit biosynthesis of angiotensin II (AII), and can be used as a safe prophylactic or therapeutic agent for various diseases caused by RA system.

Similarly, the aforementioned type A crystal, 1-(4-methoxybutyl)-N-(2-methylpropyl)-N-[(3S,5R)-5-(morpholin-4-ylcarbonyl)piperidin-3-yl]-1H-benzimidazole-2-carboxamide methanesulfonate (hereinafter to be referred to as compound X), and 1-(4-methoxybutyl)-N-(2-methylpropyl)-N-[(3S,5R)-5-(morpholin-4-ylcarbonyl)piperidin-3-yl]-1H-benzimidazole-2-carboxamide (hereinafter to be referred to as compound Y) can also be used as a safe prophylactic or therapeutic agent for various diseases caused by RA system.

Examples of the various diseases caused by RA system include hypertension (e.g., essential hypertension, renovascular hypertension, renal parenchymal hypertension, primary aldosteronism, Cushing's syndrome etc.), circadian blood pressure abnormality, cardiac disease (e.g., cardiac hypertrophy, acute cardiac failure, chronic cardiac failure including congestion, diastolic heart failure, cardiomyopathy, angina pectoris, myocarditis, atrial fibrillation, arrhythmia, tachycardia, myocardial infarction etc.), cerebrovascular disorder (e.g., asymptomatic cerebrovascular disorder, transient cerebral ischemic attack, cerebrovascular dementia, hypertensive encephalopathy, cerebral infarction etc.), brain edema, brain circulation disorder, recurrence and sequelae of cerebrovascular disorder (e.g., neural symptoms, mental symptoms, subjective symptoms, activities of daily living impairment etc.), ischemic peripheral circulation disorder, myocardial ischemia, venous insufficiency, cardiac failure progress after myocardial infarction, renal diseases (e.g., nephritis, glomerulonephritis, glomerulosclerosis, renal failure, nephrosis syndrome, thrombotic microangiopathy, dialysis complications, organ disorder including nephropathy due to radiation exposure etc.), arteriosclerosis including atherosclerosis (e.g., aneurysm, coronary sclerosis, cerebral arterial sclerosis, peripheral arterial sclerosis etc.), vascular hypertrophy, vascular hypertrophy or occlusion and organ disorder after intervention (e.g., percutaneous transluminal coronary angioplasty, stenting, coronary angioscopy, intravascular ultrasound, intracoronary thrombolytic therapy etc.), blood vessel reocclusion•restenosis after bypass surgery, polycythemia•hypertension•organ disorder•vascular hypertrophy of post-transplantation, rejection of post-transplantation, ophthalmic diseases (e.g., glaucoma, ocular hypertension etc.), thrombosis, multiple organ failure, endothelial dysfunction, hypertensive tinnitus, the other circulatory diseases (e.g., deep vein thrombosis, obstructive peripheral circulation disorder, arteriosclerosis obliterans, thromboangiitis obliterans, ischemic cerebral circulatory disorder, Raynaud's disease, Buerger's disease etc.), metabolism•malnutrition (e.g., diabetes, impaired glucose tolerance, insulin resistance, hyperinsulinemia, diabetic nephropathy, diabetic retinopathy, diabetic neuropathy, obesity, hyperlipidemia, hypercholesterolemia, hyperuricemia, hyperkalemia, hypernatremia etc.), metabolic syndrome, nonalcoholic steatohepatitis (nonalcoholic steatohepatitis, NASH), nonalcoholic fatty liver diseases (nonalcoholic fatty liver disease, NAFLD), neurodegenerative disease (e.g., Alzheimer's disease, Parkinson's disease, Creutzfeldt-Jakob disease, multiple sclerosis, amyotrophic lateral sclerosis, AIDS encephalopathy etc.), central nervous disorders (e.g., disorders such as cerebral hemorrhage, cerebral infarction and the like, and sequelae•complications thereof, head trauma, spinal injury, brain edema, disorders of sensory function, abnormality of sensory function, disorders of autonomic nervous function, abnormality of autonomic nervous function etc.), dementia, migraine, memory disorders, disturbance of consciousness, amnesia, anxiety, tension symptom, anxious mental state, sleep disorder, insomnia, mental diseases (e.g., depression, epilepsy, alcohol dependence etc.), inflammatory disease (e.g., arthritis such as rheumatoid arthritis, osteoarthritis, rheumatoid myelitis, periostitis and the like; inflammation after surgery•trauma; regression of puffiness; pharyngitis; bladder inflammation; pneumonia; atopic dermatitis; inflammatory bowel disease such as Crohn's disease, ulcerative colitis and the like; meningitis; inflammatory ocular disease; inflammatory pulmonary diseases such as pneumonia, silicosis, lung sarcoidosis, pulmonary tuberculosis and the like etc.), allergic disease (e.g., allergic rhinitis, conjunctivitis, gastrointestinal allergy, pollinosis, anaphylaxis etc.), chronic obstructive pulmonary diseases, interstitial pneumonia, carinii pneumonia, collagen disease (e.g., systemic lupus erythematosus, scleroderma, polyarteritis etc.), liver disease (e.g., hepatitis including chronic stage, cirrhosis etc.), portal hypertension, digestive tract diseases (e.g., gastritis, gastric ulcer, gastric cancer, postgastrostomy disturbances, dyspepsia, esophageal ulcer, pancreatitis, colon polyp, cholelithiasis, hemorrhoids, variceal rupture of esophagus and stomach etc.), blood•hematopoietic organ disease (e.g., polycythemia, vascular peliosis, autoimmune hemolytic anemia, disseminated intravascular coagulation syndrome, multiple myelosis etc.), bone disease (e.g., bone fracture, bone refracture, osteoporosis, osteomalacia, bone Paget's disease, rigid myelitis, rheumatoid arthritis, knee osteoarthritis and destruction of articular tissue in disease similar thereto etc.), solid tumor, tumor (e.g., malignant melanoma, malignant lymphoma, gastrointestinal (e.g., stomach, bowels etc.) cancer etc.), cancer and cachexia associated therewith, cancer metastasis, endocrine diseases (e.g., Addison's disease, pheochromocytoma etc.), urinary organs•male genital disease (e.g., bladder inflammation, prostatomegaly, prostate cancer, sexually-transmitted diseases etc.), gynecologic diseases (e.g., menopausal disorder, gestational toxicosis, endometriosis, hysteromyoma, ovarian disease, mammary gland disease, sexually-transmitted diseases etc.), disease due to environment•occupational factor (e.g., radiation disorder, disorder due to UV•infrared•laser beam, altitude sickness etc.), respiratory diseases (e.g., cold syndrome, pneumonia, asthma, pulmonary hypertension, pulmonary thrombus•pulmonary embolism etc.), infections (e.g., virus infections such as cytomegalovirus, influenza virus, herpes virus and the like, rickettsial infections, bacterium infections etc.), toxemia (e.g., sepsis, septic shock, endotoxin shock, gram negative sepsis, toxic shock syndrome etc.), otorhinolaryngologic diseases (e.g., Ménierè syndrome, tinnitus, gustation disorder, dizziness, dysequilibrium, dysphagia etc.), dermatic diseases (e.g., keloid, hemangioma, psoriasis etc.), ophthalmic diseases (e.g., cataract, glaucoma etc.), systemic disease such as dialysis hypotension, myasthenia gravis, chronic fatigue syndrome etc. and the like.

The various diseases caused by RA system also include circulatory diseases, various organ disorders caused by hypertension and the like.

The circulatory diseases include, for example, hypertension, circadian blood pressure abnormality, cardiac disease, cerebrovascular disorder, brain edema, brain m circulation disorder, recurrence and sequelae of cerebrovascular disorder, ischemic peripheral circulation disorder, myocardial ischemia, venous insufficiency, cardiac failure progress after myocardial infarction, renal diseases, arteriosclerosis including atherosclerosis, vascular hypertrophy, vascular hypertrophy or occlusion and organ disorder after intervention, blood vessel reocclusion•restenosis after bypass surgery, post-transplantation hypertension•organ disorder•vascular hypertrophy, thrombosis, multiple organ failure, endothelial dysfunction, hypertensive tinnitus, migraine, blood•hematopoietic organ disease, dialysis hypotension and the like.

The various organ disorders caused by hypertension include cardiac disease, encephalopathy, renal diseases, multiple organ failure and the like.

The crystal of the present invention shows low toxicity and can be safely administered orally or parenterally (e.g., intravenous, intramuscular, subcutaneous, intraorgan, intranasal, intradermal, ocular instillation, intracerebral, intrarectal, vaginal, intraperitoneal and intratumoral administrations, administration to the vicinity of tumor and direct administration to the lesion), as such or in the form of pharmaceutical compositions formulated with a pharmacologically acceptable carrier, e.g., tablets (including sugar-coated tablets, film-coated tablets, sublingual tablets, orally disintegrating tablets, buccal tablets etc.), pills, powders, granules, capsules (including soft capsules and microcapsule), troches, syrup, liquids, emulsion, suspension, controlled-release preparations (e.g., immediate-release preparation, controlled-release preparation, sustained-release microcapsule), aerosols, films (e.g., orally disintegrating films, oral mucosal adhesive films), injections (e.g., subcutaneous injection, intravenous injection, intramuscular injection, intraperitoneal injection), drops, transdermal absorption type preparation, ointments, lotions, patches, suppositories (e.g., rectal suppository, vaginal suppository), pellet, nasal preparations, pulmonary preparation (inhalations), eye drops and the like, in accordance with a commonly known method (e.g., the method described in the Japanese Pharmacopoeia sixteenth edition etc.).

The dose of the crystal in the pharmaceutical composition of the present invention is about 0.01 to 100% by weight relative to the entire composition. Varying depending on subject of administration, route of administration, target disease etc., its dose is normally about 1 to about 500 mg/day, preferably about 5 to about 250 mg/day, more preferably about 5 to about 100 mg/day, based on the active ingredient, for example, when it is orally administered as a rennin inhibitory agent to an adult patient (body weight: 60 kg) affected with hypertension. The crystal of the present invention may be administered once daily or in 2 to 3 divided portions per day.

Pharmacologically acceptable carriers that may be used to produce the pharmaceutical composition of the present invention include various organic or inorganic carrier substances in common use as pharmaceutical materials, for example, including excipients, lubricants, binders, disintegrants, water-soluble polymers for solid preparations; and solvents, solubilizing agents, suspending agents, isotonizing agents, buffers and soothing agents for liquid preparations. Other ordinary pharmaceutical additives such as preservatives, antioxidants, colorants, sweetening agents, acidulants, bubbling agents and flavorings may also be used as necessary.

Such "excipients" include, for example, lactose, sucrose, D-mannitol; starch, cornstarch, microcrystalline cellulose, light anhydrous silicic acid and titanium oxide.

Such "lubricants" include, for example, magnesium stearate, sucrose ester of fatty acids, polyethylene glycol, talc and stearic acid.

Such "binders" include, for example, hydroxypropyl cellulose, hydroxypropyl methyl cellulose, microcrystalline cellulose, α-starch, polyvinylpyrrolidone, gum arabic powder, gelatin, pullulan and low-substitutional hydroxypropyl cellulose.

Such "disintegrants" include (1) crospovidone, (2) disintegrants called super-disintegrants such as croscarmellose sodium (produced by FMC-Asahi Chemical) and carmellose calcium (produced by GOTOKU CHEMICAL CO., LTD.), (3) sodium carboxymethyl starch (e.g., product of Matsutani Chemical), (4) low-substituted hydroxypropyl cellulose (e.g., product of Shin-Etsu Chemical), (5) cornstarch, and so forth. Said "crospovidone" may be any crosslinked polymer having the chemical name 1-ethenyl-2-pyrrolidinone homopolymer, including polyvinylpolypyrrolidone (PVPP) and 1-vinyl-2-pyrrolidinone homopolymer, and is exemplified by Kollidon CL (produced by BASF), Polyplasdone XL (produced by ISP), Polyplasdone XL-10 (produced by ISP) and Polyplasdone INF-10 (produced by ISP).

Such "water-soluble polymers" include, for example, ethanol-soluble water-soluble polymers [e.g., cellulose derivatives such as hydroxypropyl cellulose (hereinafter also referred to as HPC), polyvinylpyrrolidone] and ethanol-insoluble water-soluble polymers [e.g., cellulose derivatives such as hydroxypropyl methyl cellulose (hereinafter also referred to as HPMC), methyl cellulose and sodium carboxymethyl cellulose, sodium polyacrylate, polyvinyl alcohol, sodium alginate, guar gum].

Such "solvents" include, for example, water for injection, alcohol, propylene glycol, macrogol, sesame oil, corn oil and olive oil.

Such "solubilizing agents" include, for example, polyethylene glycol, propylene glycol, D-mannitol, benzyl benzoate, ethanol, tris aminomethane, cholesterol, triethanolamine, sodium carbonate and sodium citrate.

Such "suspending agents" include, for example, surfactants such as stearyltriethanolamine, sodium lauryl sulfate, laurylaminopropionic acid, lecithin, benzalkonium chloride, benzethonium chloride and glyceryl monostearate; and hydrophilic polymers such as polyvinyl alcohol, polyvinylpyrrolidone, sodium carboxymethyl cellulose, methyl cellulose, hydroxymethyl cellulose, hydroxyethyl cellulose and hydroxypropyl cellulose.

Such "isotonizing agents" include, for example, glucose, D-sorbitol, sodium chloride, glycerol and D-mannitol.

Such "buffers" include, for example, buffer solutions of phosphates, acetates, carbonates, citrates etc.

Such "soothing agents" include, for example, benzyl alcohol.

Such "preservatives" include, for example, p-oxybenzoic acid esters, chlorobutanol, benzyl alcohol, phenethyl alcohol, dehydroacetic acid and sorbic acid.

Such "antioxidants" include, for example, sulfite, ascorbic acid and α-tocopherol.

Such "colorants" include, for example, food colors such as Food Color Yellow No. 5, Food Color Red No. 2 and Food Color Blue No. 2; and food lake Colors and red iron oxide.

Such "sweetening agents" include, for example, saccharin sodium, dipotassium glycyrrhizinate, aspartame, stevia and thaumatin.

Such "acidulants" include, for example, citric acid (anhydrous citric acid), tartaric acid and malic acid.

Such "bubbling agents" include, for example, sodium bicarbonate.

Such "flavorings" may be synthetic substances or naturally occurring substances, and include, for example, lemon, lime, orange, menthol and strawberry.

The crystal of the present invention may be prepared as a preparation for oral administration in accordance with a commonly known method, by, for example, compression molding it in the presence of an excipient, a disintegrant, a binder, a lubricant, or the like, and subsequently coating it as necessary by a commonly known method for the purpose of taste masking, enteric dissolution or sustained release. The "enteric coating layer" includes, for example, aqueous enteric polymer bases such as cellulose acetate phthalate (CAP), hydroxypropyl methyl cellulose phthalate, hydroxymethyl cellulose acetate succinate, methacrylic acid copolymers [e.g., Eudragit L30D-55 (trade name; produced by Röhm), Kollicoat MAE30DP (trade name; produced by BASF), Polyquid PA30 (trade name; produced by Sanyo Chemical)], carboxymethyl ethyl cellulose and shellac; sustained-release bases such as methacrylic acid copolymers [e.g., Eudragit NE30D (trade name), Eudragit RL30D (trade name), Eudragit RS30D (trade name), etc.]; water-soluble polymers;

plasticizers such as triethyl citrate, polyethylene glycol, acetylated monoglycerides, triacetin and castor oil; and mixtures thereof.

The crystal of the present invention can be formulated into solid preparations such as tablets and the like according to, for example, the method described in WO 2006/132440.

The crystal of the present invention, type A crystal, compound X and compound Y can also be used in combination with other drugs. As a drug usable in combination with the crystal of the present invention, type A crystal, compound X and compound Y (hereinafter to be abbreviated as concomitant drug), for example, the following can be used.

(1) Antihypertensive Agent

Angiotensin-converting enzyme inhibitor (e.g., captopril, enalapril maleate, alacepril, delapril hydrochloride, imidapril hydrochloride, quinapril hydrochloride, cilazapril, temocapril hydrochloride, trandolapril, benazepril hydrochloride, perindopril, lisinopril, ramipril etc.), angiotensin II antagonist (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil etc.), aldosterone receptor antagonists (spironolactone, eplerenone etc.), calcium antagonist (e.g., verapamil hydrochloride, diltiazem hydrochloride, nifedipine, amlodipine besilate, azelnidipine, aranidipine, efonidipine hydrochloride, cilnidipine, nicardipine hydrochloride, nisoldipine, nitrendipine, nilvadipine, barnidipine hydrochloride, felodipine, benidipine hydrochloride, manidipine hydrochloride etc.), β blocker (e.g., metoprolol tartrate, atenolol, propranolol hydrochloride, bisoprolol fumarate etc.), αβ blocker (carvedilol etc.), clonidine, diuretic (theobromine sodium salicylate, theobromine calcium salicylate, ethiazide, cyclopenthiazide, trichlormethiazide, hydrochlorothiazide, hydroflumethiazide, benzylhydrochlorothiazide, penfluthiazide, poly5thiazide, methyclothiazide, acetazolamide, tripamide, meticrane, chlorthialidone, mefruside, indapamide, azosemide, isosorbide, ethacrynic acid, piretanide, bumetanide, furosemide etc.) and the like.

(2) Antithrombotic Agent

Anticoagulant (e.g., heparin sodium, heparin calcium, warfarin calcium (warfarin), anti-thrombin drug (e.g., argatroban, dabigatran etc.), activated blood coagulation factor Xa inhibitor and medicament having function redressing the balance of coagulation fibrinolytic system (e.g., rivaroxaban, apixaban, edoxaban, YM-150, the compound described in WO 02/06234, WO 2004/048363, WO 2005/030740, WO 2005/058823, WO 2005/113504 or WO 2004/048363 etc.) etc.), thrombolytic drug (e.g., tPA, urokinase, tisokinase, alteplase, nateplase, monteplase, pamiteplase), antiplatelet drug (e.g., aspirin, sulfinpyrazone (anturane), dipyridamole (persantine), ticlopidine hydrochloride (panaldine), cilostazol (pletal), GPIIb/IIIa antagonist (e.g., ReoPro etc.), clopidogrel, prasugrel, ticagrelor, E5555, SHC530348, ethyl icosapentate, beraprost sodium, sarpogrelate hydrochloride etc.) and the like.

(3) Therapeutic Agent for Diabetes

Insulin preparation (e.g., animal insulin preparation extracted from pancreas of bovine and swine; human insulin preparation genetic engineering-synthesized using *Escherichia coli* and yeast; zinc insulin; protamine zinc insulin; insulin fragment or derivative (e.g., INS-1), oral insulin preparation etc.), insulin sensitizer (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, the compound described in WO 2007/013694, WO 2007/018314, WO 2008/093639 or WO 2008/099794 etc.), α-glucosidase inhibitor (e.g., voglibose, acarbose, miglitol, emiglitate etc.), biguanide (e.g., phenformin, metformin, buformin or a salt thereof (e.g., hydrochloride, fumarate, succinate etc.) etc.), insulin secretagogue (e.g., sulfonylurea (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or a calcium salt hydrate thereof etc.), dipeptidyl peptidase IV inhibitor (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1 (2H)-pyrimidinyl]methyl]-4-fluorobenzonitrile or a salt thereof), β3 agonist (e.g., N-5984), GPR40 agonist (e.g., the compound described in WO 2004/041266, WO 2004/106276, WO 2005/063729, WO 2005/063725, WO 2005/087710, WO 2005/095338, WO 2007/013689 or WO 2008/001931 etc.), GLP-1 receptor agonist (e.g., GLP-1, GLP-1MR agent, Liraglutide, Exenatide, AVE-0010, BIM-51077, Aib(8,35) hGLP-1(7,37)NH$_2$, CJC-1131, Albiglutide, amylin agonist (e.g., pramlintide etc.), phosphotyrosine phosphatase inhibitors (e.g., sodium vanadate etc.), gluconeogenesis inhibitor (e.g., glycogen phosphorylase inhibitor, glucose-6-phosphatase inhibitors, glucagon antagonists, FBPase inhibitor etc.), SGLT2 (sodium-glucose cotransporter 2) inhibitor (e.g., Depagliflozin, AVE2268, TS-033, YM543, TA-7284, Remogliflozin, ASP1941 etc.), SGLT1 inhibitor, 11β-hydroxy steroid dehydrogenase inhibitor (e.g., BVT-3498, INCB-13739 etc.), adiponectin or an agonist thereof, IKK inhibitor (e.g., AS-2868 etc.), leptin resistance improving drugs, somatostatin receptor agonists, glucokinase activators (e.g., Piragliatin, AZD1656, AZD6370, TTP-355, the compound described in WO 2006/112549, WO 2007/028135, WO 2008/047821, WO 2008/050821, WO 2008/136428 or WO 2008/156757 etc.), GIP (Glucose-dependent insulinotropic peptide), GPR119 agonist (e.g., PSN821 etc.), FGF21, FGF analogue and the like.

(4) Therapeutic Agents for Diabetic Complications

Aldose reductase inhibitors (e.g., tolrestat, epalrestat, zopolrestat, fidarestat, CT-112, ranirestat (AS-3201), Lidorestat etc.), neurotrophic factor and an increasing drug thereof (e.g., NGF, NT-3, BDNF, neurotrophic factors and increasing drugs thereof described in WO 01/14372 (e.g., 4-(4-chlorophenyl)-2-(2-methyl-1-imidazolyl)-5-[3-(2-methylphenoxy)propyl]oxazole etc.), the compound described in WO 2004/039365 etc.), PKC inhibitor (e.g., ruboxistaurin mesylate etc.), AGE inhibitor (e.g., ALT946, N-phenacylthiazolium bromide (ALT766), EXO-226, Pyridorin, pyridoxamine etc.), GABA receptor agonist (e.g., gabapentin, Pregabalin etc.), serotonin•noradrenaline reuptake inhibitor (e.g., duloxetine etc.), sodium channel inhibitor (e.g. Lacosamide etc.), active oxygen scavengers (e.g., thioctic acid etc.), cerebral vasodilator (e.g., tiapuride, mexiletine etc.), somatostatin receptor agonists (e.g., BIM23190 etc.), apoptosis signal regulating kinase-1 (ASK-1) inhibitor and the like.

(5) Antilipidemic Agent

HMG-CoA reductase inhibitor (e.g., pravastatin, simvastatin, lovastatin, atorvastatin, fluvastatin, rosuvastatin, pitavastatin or a salt thereof (e.g., sodium salt, calcium salt etc.) etc.), squalene synthase inhibitors (e.g., the compound described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid etc.), fibrate compound (e.g., bezafibrate, clofibrate, simfibrate, clinofibrate etc.), anion exchange resin (e.g., colestyramine etc.), probucol, nicotinic acid drugs (e.g., nicomol, niceritrol, niaspan etc.), ethyl icosapentate, phytosterol (e.g., soysterol, γ-oryzanol etc.), cholesterol absorption inhibitor (e.g., Zetia etc.), CETP inhibitor (e.g., dalcetrapib, anacetrapib etc.), ω-3 fatty acid preparation (e.g., ω-3-acid ethyl esters 90 etc.) and the like.

Besides the above, they can be used in combination with other pharmaceutical ingredients including therapeutic drugs for bone diseases, myocardial protective drugs, therapeutic drugs for coronary heart diseases, therapeutic drugs for chronic cardiac failure, therapeutic drugs for hypothyroidism, therapeutic drugs for nephrosis syndrome, therapeutic drugs for chronic renal failure, therapeutic agents for renal anemia (e.g., erythropoietin preparation, peginesatide etc.), therapeutic drugs for gynecologic diseases and therapeutic drugs for infections. The drug to be used in combination may be an antibody drug or a nucleic acid drug, and the crystal of the present invention, type A crystal, compound X and compound Y can also be used along with a gene therapy.

The medicament of the present invention wherein the crystal of the present invention and a concomitant drug are mixed or used in combination also includes both (1) a medicament formulated as a single pharmaceutical composition containing the crystal of the present invention and a concomitant drug, and (2) a medicament containing a pharmaceutical composition containing the crystal of the present invention and a concomitant drug, which are formulated separately. In the following, they are collectively abbreviated as "the concomitant agent of the present invention".

Similarly, the medicament wherein type A crystal, compound X and compound Y, and a concomitant drug are mixed or used in combination also includes both (1) a medicament formulated as a single pharmaceutical composition containing type A crystal, compound X and compound Y, and a concomitant drug, and (2) a medicament containing a pharmaceutical composition containing type A crystal, compound X and compound Y and a concomitant drug, which are formulated separately. In the following, they are collectively abbreviated as "concomitant agent Z".

The concomitant agent and concomitant agent Z of the present invention can be formulated separately or simultaneously, as such or by mixing the crystal of the present invention and the active ingredient of the concomitant drug with a pharmaceutically acceptable carrier and the like, according to a method similar to the method for the aforementioned solid preparation of the present invention.

While the daily dose of the concomitant agent of the present invention varies depending on the symptom, race, age, sex and body weight of the administration subject, administration form, kind of the active ingredient and the like, it is not particularly limited as long as the side effect does not pose problems. For example, the daily dose of the concomitant agent of the present invention for oral administration is generally about 0.005-about 100 mg, preferably about 0.05-about 50 mg, more preferably about 0.2-about 4 mg, as the total dose of the crystal of the present invention and a concomitant drug, per 1 kg/body weight of a mammal, and this amount is generally administered in 1 to 3 portions a day.

In administration of a combination agent of the present invention, the crystal of the present invention may be administered after administration of the concomitant drug or the concomitant drug may be administered after administration of the crystal of the present invention, though they may be administered simultaneously. When administered at a time interval, the interval differs depending on the effective ingredient to be administered, drug form and administration method, and for example, when the concomitant drug is administered first, a method in which the crystal of the present invention is administered within time range of from 1 min to 3 days, preferably from 10 min to 1 day, more preferably from 15 min to 1 hr after administration of the concomitant drug is exemplified. When the crystal of the present invention is administered first, a method in which the concomitant drug is administered within time range of from 1 min to 1 day, preferably from 10 min to 6 hrs, more preferably from 15 min to 1 hr after administration of the crystal of the present invention is exemplified. As a method for administering concomitant agent Z, a similar method can be mentioned.

In the concomitant agent of the present invention, the content of the crystal of the present invention in the whole concomitant agent varies depending on the form of the concomitant agent, and is generally about 0.1 wt %-65 wt %, preferably 0.3 wt %-50 wt %, more preferably 0.5 wt %-20 wt %.

EXAMPLES

The present invention is explained in detail in the following by referring to Reference Examples and Examples, which are not to be construed as limitative.

In the following Reference Examples and Examples, the ratio shown for mixed solvents is a volume ratio unless otherwise specified. % shows wt % unless otherwise specified.

The powder X-ray diffraction of type A crystal was measured using X-RAY DIFFRACTOMETER RINT2000 (Rigaku), and the powder X-ray diffraction of type B crystal was measured using RINT2500V (Rigaku).

The hydrochloric acid content was measured using ion chromatography (manufactured by DIONEX).

The abbreviations in Reference Examples and Examples mean as follows.

s: singlet, d: doublet, t: triplet, q: quartet, dd: double doublet, dt: double triplet, m: multiplet, br: broad, tt: triple triplet, and J: coupling constant Reference Example A tert-butyl(3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate tert-Butyl(3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate is obtained according to the method described in Reference Example 146 of WO 2009/154300.

tert-Butyl(3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate is dissolved in toluene. The solution is heated to 35-45° C., heptane is added dropwise, and the mixture is stirred for 30 min or longer. The mixture is allowed to cool to 20-30° C. and stirred for 2 hr. The precipitated crystals are collected by filtration and washed with toluene-heptane. The crystals are dried under reduced pressure at 50° C. to give tert-butyl(3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate as crystals.

Reference Example 1

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type A crystal)

tert-Butyl(3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate (300 g) was suspended/dissolved in 3N hydrochloric acid (1200 mL) and ethyl acetate (60 mL), and the mixture was stirred at 25-35° C.

for 3 hr or longer. After completion of the reaction, ethyl acetate (2400 mL) was added at the same temperature. After the addition, 25% aqueous ammonia (600 mL) was added with cooling. After addition with stirring, 5% aqueous ammonia (600 mL) was added to the extracted organic layer and the mixture was stirred. After stirring, the obtained organic layer was concentrated until the solvent ceased to evaporate. After concentration, the concentrate was dissolved in ethyl acetate (1500 mL), the dissolved solution was placed in a crystallization vessel, and the used container was washed with ethyl acetate (750 mL). After washing, the mixture was heated to 45-55° C. with stirring. After heating, 4N hydrogen chloride-ethyl acetate (131.3 mL) was added dropwise at the same temperature. After the dropwise addition, the precipitate was dissolved at the same temperature. After the dissolution was confirmed, heptane (750 mL) was added at 40-50° C., and after the addition, the mixture was allowed to cool to 25-35° C. After cooling, the seed crystals (300 mg) of type A crystal obtained according to the method described in Example 265 of WO 2009/154300 was added, and the mixture was stirred for 30 min or longer. After stirring, the mixture was heated to 40-45° C., and heptane (1500 mL) was added dropwise. After completion of the dropwise addition, the mixture was stirred at the same temperature. Then, the mixture was slowly cooled to 5° C. or lower, and stirred at the same temperature for 1 hr. After stirring, the crystals were collected by filtration and washed with ethyl acetate-heptane (1:1, 600 mL) to give wet crystals. The obtained wet crystals were dried under reduced pressure at 50° C. to give 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a crystalline powder (type A crystal, 198.82 g, yield 74.1%).

Reference Example 2

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type A crystal)

1-(4-Methoxybutyl)-N-(2-methylpropyl)-N-[(3S,5R)-5-(morpholin-4-ylcarbonyl)piperidin-3-yl]-1H-benzimidazole-2-carboxamide methanesulfonate monohydrate (1500 g) was dissolved in water (7500 mL). Sodium bicarbonate water ($NaHCO_3$ 411 g, water 7500 mL) prepared in advance was added to the dissolved solution, and the mixture was stirred. Under stirring, ethyl acetate (15000 mL) was added and the mixture was stirred. After stirring, ethyl acetate (15000 mL) was added to the extracted aqueous layer and the mixture was stirred. After stirring, ethyl acetate (15000 mL) was added to the extracted aqueous layer again and the mixture was stirred. The obtained organic layer was combined, and the mixture was concentrated to about 8 L. Ethyl acetate (10000 mL) was added to the concentrated solution, and the mixture was concentrated to about 8 L. The concentrated solution was left standing overnight. To the concentrated solution left standing overnight was added ethyl acetate (10000 mL), and the mixture was concentrated to about 8 L. To the concentrated solution was added ethyl acetate (12500 mL), and the mixture was heated to 45-55° C. with stirring. After the temperature rise, 4N hydrogen chloride-ethyl acetate (730 mL) was added dropwise. After dropwise addition, the precipitate was dissolved. After the dissolution was confirmed, heptane (6000 mL) was added, and the mixture was allowed to cool to 35-40° C. After cooling, the seed crystals (1.5 g) of type A crystal obtained according to the method described in Reference Example 3 was added, and heptane (12800 mL) was added dropwise at the same temperature. After the completion of the dropwise addition, the mixture was heated to 40-50° C. and stirred for 1 hr or longer. After stirring, the mixture was allowed to cool to 20-30° C. and stirred for 1 hr or longer at the same temperature. After stirring, the crystals were collected by filtration and washed with ethyl acetate-heptane (1:1, 4600 mL) to give wet crystals. The obtained wet crystals were dried under reduced pressure at 50° C. to give 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a crystalline powder (type A crystal, 1195 g, yield 91.2%).

Reference Example 3

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type A crystal)

1-(4-Methoxybutyl)-N-(2-methylpropyl)-N-[(3S,5R)-5-(morpholin-4-ylcarbonyl)piperidin-3-yl]-1H-benzimidazole-2-carboxamide hydrochloride (type A crystal, 190 g) was suspended in 2-propanol-ethyl acetate (1:7.5, 2153 mL). Then, the mixture was dissolved by heating to 40-50° C. After the dissolution was confirmed, heptane (1330 mL) was added dropwise. Then, the seed crystals (190 mg) of type A crystal obtained according to the method described in Example 265 of WO 2009/154300 was added, and heptane (570 mL) was added dropwise. After stirring, the mixture was allowed to cool to 25-30° C. and stirred for 1 hr. After stirring, the mixture was heated to 40-50° C. and stirred for 1 hr. After stirring, the mixture was allowed to cool to 20-25° C. and stirred at the same temperature for 1 hr. After stirring, the crystals were collected by filtration and washed with ethyl acetate-heptane (1:1, 570 mL) to give wet crystals. The obtained wet crystals were dried under reduced pressure at 50° C. to give a crystalline powder having a powder X-ray diffraction pattern showing characteristic peaks at lattice spacings (d) of around 17.18, 12.27, 8.73, 7.13, 4.76 angstroms (type A crystal, 155.7 g, yield 81.9%). The measurement results of the powder X-ray diffraction are shown in the following Table.

TABLE 1

| Powder X-ray diffraction data (type A crystal) | | |
|---|---|---|
| 2θ (°) | d value (Å) | relative intensity (%) |
| 5.14 | 17.18 | 100 |
| 7.20 | 12.27 | 25 |
| 10.12 | 8.73 | 43 |
| 12.40 | 7.13 | 59 |
| 18.64 | 4.76 | 100 |

As a result of a hydrochloric acid content analysis, the above-mentioned hydrochloride was confirmed to be monohydrochloride.

theoretical hydrochloric acid content 6.8%, measured value 6.8%

Reference Example 4 tert-butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate 1) Toluene (500 mL) was added to o-nitroaniline (50.0 g, 0.362 mol), tetrabutylammonium bromide (58.3 g, 0.181 mol) and potassium bromide (43.1 g, 0.362 mol). 1-Chloro-4-methoxybutane (66.6 g, 0.543 mol) and 50 w/v % aqueous sodium hydroxide solution (145 mL, 1.81 mol) were added at 20-30° C. The reaction mixture was heated to 85-95° C., and stirred for 6 hr. After allowing to cool to 20-30° C., the reaction mixture was washed successively with water (250 mL), 1N hydrochloric acid (250 mL×2), 5 w/v % sodium bicarbonate water (250 mL) and water (250 mL). The organic layer was concentrated under reduced pressure to the content (250 mL), and toluene (100 mL) was added to give a toluene solution (350 mL) of N-(4-methoxybutyl)-2-nitroaniline (yield 100%).

$^1$H-NMR (300 MHz, CDCl$_3$) δ 1.64-1.89 (m, 4H), 3.25-3.39 (m, 2H), 3.35 (s, 3H), 3.44 (t, J=6.1 Hz, 2H), 6.63 (ddd, J=8.5, 6.9, 1.2 Hz, 1H), 6.86 (dd, J=8.5, 1.2 Hz, 1H), 7.43 (ddd, J=8.5, 6.9, 1.5 Hz, 1H), 8.07 (br s, 1H), 8.17 (dd, J=8.5, 1.5 Hz, 1H).

2) To a toluene solution (350 mL) of N-(4-methoxybutyl)-2-nitroaniline were added 10% Pd/C (K-type, 50% water-containing product, 10.0 g) and toluene (100 mL). The mixture was stirred at 20-30° C. for 3 hr under a hydrogen pressure (0.1 MPa). Under a nitrogen stream, the catalyst was filtered off and the residue was washed with toluene (100 mL). Water in the filtrate was removed by partitioning, magnesium sulfate (25.0 g) was added at 20-30° C., and the mixture was stirred at the same temperature for 30 min. Magnesium sulfate was filtered off and the residue was washed with toluene (100 mL) to give a toluene solution of N-(4-methoxybutyl)-o-phenylenediamine (yield 100%).

$^1$H NMR (500 MHz, CDCl$_3$) δ1.67-1.78 (m, 4H), 3.12-3.14 (m, 2H), 3.32 (br, 3H), 3.35 (s, 3H), 3.41-3.47 (m, 2H), 6.63-6.69 (m, 2H), 6.69-6.74 (m, 1H), 6.82 (td, J=7.57, 1.58 Hz, 1H).

3) A solution of N-(4-methoxybutyl)-o-phenylenediamine in toluene was cooled to 0-10° C., and acetic acid (65.2 g, 1.09 mol) and methyl 2,2,2-trichloroacetimidate (70.3 g, 0.398 mol) were added. After stirring at 0-10° C. for 30 min, the mixture was stirred at 20-30° C. for 3 hr. The reaction mixture was successively washed with 5 w/v % brine (250 mL), a mixed solution of 2N hydrochloric acid/5 w/v % brine (1:1, 250 mL×2), 5 w/v % sodium bicarbonate water (250 mL) and 5 w/v % brine (250 mL). Under a nitrogen stream, magnesium sulfate (25.0 g) was added to the organic layer at 20-30° C., and the mixture was stirred at the same temperature for 30 min. Magnesium sulfate was filtered off and the residue was washed with toluene (100 mL). The filtrate was concentrated under reduced pressure to give the content (150 mL). The concentrated solution was stirred at 20-30° C., the crystals were precipitated, and heptane (750 mL) was added dropwise. The crystallized solution was heated to 40-50° C. and stirred for 30 min. After stirring, the solution was cooled to 0-10° C. and stirred at the same temperature for 2 hr. The precipitated crystals were collected by filtration, washed with toluene-heptane (1:5, 150 mL) and dried under reduced pressure at 40° C. to give 1-(4-methoxybutyl)-2-trichloromethyl-1H-benzimidazole as pale brown crystals (96.5 g, yield 82.9% from o-nitroaniline).

$^1$H-NMR (300 MHz, CDCl$_3$) δ: 1.68-1.85 (m, 2H), 1.99-2.17 (m, 2H), 3.37 (s, 3H), 3.48 (t, J=6.1 Hz, 2H), 4.50-4.65 (m, 2H), 7.27-7.49 (m, 4H), 7.82-7.93 (m, 1H).

Anal. Calcd for C$_{13}$H$_{15}$Cl$_3$N$_2$O: C, 48.55; H, 4.70; N, 8.71; Cl, 33.07. Found: C, 48.30; H, 4.61; N, 8.74; Cl, 33.30.

4) To a mixture of pyridine-3,5-dicarboxylic acid (110 g, 0.66 mol) and methanol (660 mL) was added dropwise conc. sulfuric acid (226.0 g, 2.30 mol) at 50° C. or lower. Thereafter, the mixture was heated to 55-65° C. and stirred for 7 hr. The reaction mixture was allowed to cool to 40-50° C., and water (220 mL) was added. Furthermore, 5% aqueous ammonia (about 1.10 L) was added dropwise at 40-50° C. to adjust the mixture to pH 8.0-8.5. After stirring at 40-50° C. for 30 min, the mixture was cooled to 0-10° C. and stirred for 1 hr. The precipitated crystals were collected by filtration, washed successively with methanol-water (1:3, 165 mL) and water (440 mL), and dried under reduced pressure at 50° C. to give dimethyl pyridine-3,5-dicarbonate as a white crystalline powder (105.0 g, yield 82.0%).

$^1$H-NMR (300 MHz, CDCl$_3$) δ 4.00 (s, 6H), 8.87 (s, 1H), 9.37 (s, 2H).

Anal. Calcd for C$_9$H$_9$NO$_4$: C, 55.39; H, 4.65; N, 7.18; O, 32.79.

Found: C, 55.42; H, 4.65; N, 7.16.

5) Dimethylpyridine-3,5-dicarbonate (100 g, 0.51 mol) and dimethylacetamide (400 mL) were charged in an autoclave (1 L), trifluoroacetic acid (59.2 mL, 0.77 mol) was added dropwise at 30° C. or lower, and 10% Pd—C (PE-type, 20.0 g) was added. The mixture was stirred at 55-65° C. for 12 hr under a hydrogen pressure (0.5-0.7 MPa). The catalyst was filtered off and the residue was washed with dimethylacetamide (50 mL×2). The filtrates were combined, and triethylamine (77.8 g, 0.77 mol) was added dropwise at 20-30° C. to adjust the mixture to pH 9.0-10.0. Di-tert-butyl bicarbonate (134 g, 0.614 mol) was added dropwise at 30-40° C., and the mixture was stirred at the same temperature for 2 hr. The reaction mixture was allowed to cool to 20-30° C., ethyl acetate (600 mL) was added, and the mixture was washed with water (900 mL). The aqueous layer was extracted again with ethyl acetate (400 mL). The organic layers were combined and washed successively with 5 w/v % citric acid-10 w/v % brine (600 mL), 3% sodium bicarbonate water (600 mL) and water (600 mL). The organic layer was concentrated under reduced pressure to the content (200 mL), methanol (250 mL) was added to the concentrated solution, and the mixture was concentrated under reduced pressure to the content (200 mL). Methanol (250 mL) was added again to the concentrated solution, the mixture was concentrated under reduced pressure to the content (200 mL), and methanol (2.40 L) was added. To this solution were added water (18.5 g, 1.03 mol) and cesium carbonate (417 g, 1.28 mol), and the mixture was stirred at 55-65° C. for about 24 hr. The reaction mixture was allowed to cool to 20-30° C. and concentrated to the content (700 mL), and tetrahydrofuran (500 mL) was added. To this solution was added dropwise 2N hydrochloric acid (1.28 L, 2.56 mol) at 15-35° C., and the mixture was adjusted to pH 3.0-3.5 and stirred at 20-30° C. for 30 min. The mixture was extracted with ethyl acetate (750 mL×2), and the organic layer was washed with 10 w/v % brine (500 mL×3). The organic layer was concentrated under reduced pressure to the content (300 mL), and ethyl acetate was added to the content (650 mL). The concentrate was heated to 55-65° C., and heptane (500 mL) was added dropwise. The mixture was allowed to cool to 20-30° C. and stirred for 1 hr. The precipitated crystals were collected by filtration, washed with ethyl acetate-heptane (1:1, 120 mL), and dried under reduced pressure at 50° C. to give 1-(tert-butoxycarbonyl)piperidine-3,5-dicarboxylic acid as a white crystalline powder (113.3 g, yield 80.9%).

$^1$H-NMR (300 MHz, DMSO-d$_6$) δ 1.40 (s, 9H), 1.44-1.61 (m, 1H), 2.21-2.26 (m, 1H), 2.31-2.41 (m, 2H), 4.10-4.12 (m, 2H).

Anal. Calcd for C$_{12}$H$_{19}$NO$_6$: C, 52.74; H, 7.01; N, 5.13; O, 35.13.

Found: C, 52.96; H, 6.99; N, 5.39.

6) Under a nitrogen stream, 1-(tert-butoxycarbonyl)piperidine-3,5-dicarboxylic acid (5.00 g, 18.3 mmol) was suspended in tetrahydrofuran (10.0 mL), and trifluoroacetic anhydride (3.80 mL, 27.5 mmol) was added dropwise at 20-30° C. After completion of the dropwise addition, the mixture was stirred at 20-30° C. for 1 hr. To the reaction mixture was added dropwise heptane (20.0 mL) at 20-30° C., and the mixture was cooled to 0-10° C. and stirred for 3 hr. The precipitated crystals were collected by filtration, washed with heptane (3.00 mL), and dried under reduced pressure at 40° C. to give tert-butyl 2,4-dioxo-3-oxa-7-azabicyclo[3,3,1] nonane-7-carboxylate as a white crystalline powder (4.03 g, yield 86.1%).

$^1$H-NMR (300 MHz, CDCl$_3$) δ 1.43 (s, 9H), 1.93-1.99 (m, 1H), 2.40-2.46 (m, 1H), 3.06-3.11 (m, 4H), 4.50-4.54 (m, 2H).

Anal. Calcd for C$_{12}$H$_{17}$NO$_5$: C, 56.46; H, 6.71; N, 5.49; O, 31.34.

Found: C, 56.51; H, 6.63; N, 5.69.

7) Under a nitrogen stream, quinidine (69.9 g, 0.215 mol) and tetrahydrofuran (200 mL) were charged and the mixture was cooled to −5 to 5° C. tert-Butyl 2,4-dioxo-3-oxa-7-azabicyclo [3,3,1]nonane-7-carboxylate (50.0 g, 0.196 mol) was added at the same temperature, and the used container was washed with tetrahydrofuran (50.0 mL). Methanol (9.41 g, 0.29 4 mol) was added dropwise at −5 to 5° C., and the mixture was stirred at −5 to 5° C. for 2 hr. To the reaction mixture were added ethyl acetate (350 mL) and 20 w/v % aqueous citric acid solution (250 mL), and the mixture was partitioned. The aqueous layer was extracted again with ethyl acetate (125 mL×2). The organic layers were combined and washed successively with 20 w/v % aqueous citric acid solution (250 mL) and water (250 mL×2). The organic layer was concentrated under reduced pressure. To the residue were added ethanol (100 mL) and ethyl acetate (450 mL), the mixture was heated to 60-70° C., and (R)-phenethylamine (23.7 g, 0.196 mol) was added. The mixture was stirred at 50-60° C. for 1 hr, at 20-30° C. for 1 hr and at −5 to 5° C. for 1 hr. The precipitated crystals were collected by filtration, washed with ethanol-ethyl acetate (2:9, 100 mL), and dried under reduced pressure at 50° C. to give (3S,5R)-1-(tert-butoxycarbonyl)-5-(methoxycarbonyl)piperidine-3-carboxylic acid (1R)-1-phenylethylamine salt as a white crystalline powder (55.7 g, yield 69.6%).

$^1$H-NMR (300 MHz, DMSO-d$_6$) δ 1.42 (s, 9H), 1.43-1.51 (m, 3H), 2.06-2.14 (m, 1H), 2.21-2.26 (m, 1H), 2.39-2.44 (m, 1H), 2.52-2.53 (m, 1H), 2.57 (br s, 2H), 3.64 (s, 3H), 4.12 (br s, 2H), 4.19-4.26 (m, 1H), 7.30-7.40 (m, 3H), 7.45-7.48 (m, 2H).

Anal. Calcd for C$_{21}$H$_{32}$N$_2$O$_6$: C, 61.75; H, 7.90; N, 6.86; O, 23.50.

Found: C, 61.54; H, 7.77; N, 6.86.

8) (3S,5R)-1-(tert-Butoxycarbonyl)-5-(methoxycarbonyl)piperidine-3-carboxylic acid (1R)-1-phenylethylamine salt (20.0 g, 49.0 mmol), methanol (20 mL) and water (80 mL) were charged. A solution of citric acid (11.3 g, 58.8 mmol) in water (20.0 mL) was added dropwise at 20-30° C., and the mixture was stirred at the same temperature for 1.5 hr. The precipitated crystals were collected by filtration, washed with water (60 mL), and dried under reduced pressure at 50° C. to give (3S,5R)-1-(tert-butoxycarbonyl)-5-(methoxycarbonyl) piperidine-3-carboxylic acid as a white crystalline powder (13.5 g, yield 96.1%).

$^1$H-NMR (300 MHz, CDCl$_3$) δ 1.40 (s, 9H), 1.46-1.59 (m, 1H), 2.22-2.27 (m, 1H), 2.37-2.45 (m, 2H), 2.63-2.73 (m, 2H), 3.63 (s, 3H), 4.14 (br s, 2H), 12.51 (br s, 1H).

Anal. Calcd for C$_{13}$H$_{21}$NO$_6$: C, 54.35; H, 7.37; N, 4.88; O, 33.41.

Found: C, 54.14; H, 7.28; N, 4.85.

9) Under a nitrogen stream, (3S,5R)-1-(tert-butoxycarbonyl)-5-(methoxycarbonyl)piperidine-3-carboxylic acid (30.0 g, 104 mmol), triethylamine (31.7 g, 313 mmol) and toluene (180 mL) were charged. A solution of diphenylphosphoryl azide (28.7 g, 313 mmol) in toluene (30.0 mL) was added dropwise at 15-35° C. After stirring at 30±5° C. for 30 min, the mixture was heated to 65-75° C. and stirred for 30 min. Benzylalcohol (12.4 g, 115 mmol) was added dropwise at 60-70° C. The mixture was heated to 80-90° C. and stirred for 3 hr. The reaction mixture was allowed to cool to 20-30° C., a solution of sodium nitrite (7.20 g, 104 mmol) in water (150 mL) was added, the mixture was stirred for 1 hr, and the aqueous layer was partitioned. The organic layer was washed successively with 5 w/v % sodium bicarbonate water (150 mL), 20 w/v % aqueous citric acid solution (150 mL) and 5 w/v % brine (150 mL), and the organic layer was concentrated under reduced pressure. To the residue was added methanol (60.0 mL), and the mixture was concentrated under reduced pressure. A similar operation was performed once more. To the residue was added methanol to give the content (90.0 g). 2N Aqueous sodium hydroxide solution (62.6 mL, 125 mmol) was added at 15-35° C., and the mixture was stirred at 30±5° C. for 1 hr. Methanol (120 mL) and 20 w/v % aqueous citric acid solution (300 mL) were added at 20-30° C. to adjust the mixture to pH 3.0-3.5. After stirring at 50-60° C. for 30 min, the mixture was allowed to cool to 20-30° C. and stirred for 1 hr. Furthermore, the mixture was stirred at 0-10° C. for 1 hr. The precipitated crystals were collected by filtration, washed with water (90.0 mL), and dried under reduced pressure at 50° C. to give (3R,5S)-5-{[(benzyloxy)carbonyl] amino}-1-(tert-butoxycarbonyl)piperidine-3-carboxylic acid as a white crystalline powder (35.0 g, yield 88.6%).

$^1$H-NMR (300 MHz, DMSO-d$_6$) δ 1.41 (s, 9H), 2.11 (d, J=12.4 Hz, 1H), 2.40-2.48 (m, 4H), 2.62 (br s, 1H), 4.08 (t, J=14.4 Hz, 2H), 5.04 (s, 2H), 7.31-7.41 (m, 5H), 12.53 (br s, 1H).

Anal. Calcd for C$_{19}$H$_{26}$N$_2$O$_6$: C, 60.30; H, 6.93; N, 7.40; O, 25.37.

Found: C, 60.03; H, 6.99; N, 7.41.

10) Under a nitrogen stream, (3R,5S)-5-{[(benzyloxy)carbonyl]amino}-1-(tert-butoxycarbonyl)piperidine-3-carboxylic acid (30.0 g, 79.3 mmol), morpholine (7.60 g, 87.2 mmol), 1-hydroxybenzotriazole monohydrate (2.43 g, 15.9 mmol) and dimethylacetamide (90.0 mL) were charged. 1-Ethyl-3-(3-dimethylaminopropyl)carbodiimide hydrochloride (16.7 g, 87.1 mmol) was added at 20-30° C., and the mixture was stirred at 45-55° C. for 1 hr. Tetrahydrofuran (90.0 mL) and water (210 mL) were successively added dropwise at 45-55° C., and the mixture was stirred for 1 hr. The mixture was allowed to cool to 20-30° C. and stirred for 1 hr, and the precipitated crystals were collected by filtration, washed with tetrahydrofuran-water (1:3, 120 mL), and dried under reduced pressure at 50° C. to give tert-butyl piperidine-1-(3S, 5R)-3-{[(benzyloxy)carbonyl]amino}-5-(morpholin-4-ylcarbonyl)carboxylate as a white crystalline powder (32.7 g, yield 92.3%).

$^1$H-NMR (300 MHz, DMSO-d$_6$) δ 1.41 (s, 9H), 1.49-1.57 (m, 1H), 1.87 (d, J=12.3 Hz, 1H), 2.43 (br s, 1H), 2.63-2.71 (m, 1H), 2.79-2.83 (m, 1H), 3.37-3.54 (m, 9H), 3.89 (d, J=11.5 Hz, 1H), 4.06 (br s, 1H), 5.03 (s, 2H), 7.30-7.38 (m, 5H).

Anal. Calcd for C$_{23}$H$_{33}$N$_3$O$_6$: C, 61.73; H, 7.43; N, 9.39; O, 21.45.

Found: C, 61.59; H, 7.50; N, 9.43.

11) tert-Butyl piperidine-(3S,5R)-3-{[(benzyloxy)carbonyl] amino}-5-(morpholin-4-ylcarbonyl)carboxylate (30.0 g, 67.0 mmol), isobutylaldehyde (7.25 g, 101 mmol), 10%

Pd—C (PE type, 1.50 g) and methanol (240 mL) were charged. The mixture was stirred at 20-30° C. for 4 hr under a hydrogen pressure (0.2-0.3 MPa). The catalyst was filtered off and the residue was washed with methanol (60.0 mL). The filtrate was concentrated under reduced pressure, ethyl acetate (60.0 mL) was added, and the mixture was concentrated again under reduced pressure. To the residue was added ethyl acetate to give the content (360 mL). The mixture was heated to 45-55° C., and succinic acid (7.90 g, 67.0 mmol) was added. The mixture was stirred at 45-55° C. for 1 hr, allowed to cool to 20-30° C., and stirred for 1 hr. The precipitated crystals were collected by filtration, washed with ethyl acetate (90.0 mL), and dried under reduced pressure at 50° C. to give tert-butyl (3S,5R)-3-[(2-methylpropyl)amino]-5-(morpholin-4-ylcarbonyl)piperidine-1-carboxylate succinate as a white crystalline powder (30.2 g, yield 92.5%).

$^1$H-NMR (300 MHz, D$_2$O) δ 1.02 (s, 3H), 1.04 (s, 3H), 1.47 (s, 9H), 1.97-2.09 (m, 2H), 2.26-2.30 (m, 1H), 2.55 (s, 4H), 2.99 (d, J=7.0 Hz, 2H), 3.23 (br s, 1H), 3.39-3.45 (m, 2H), 3.53-3.80 (m, 10H), 3.82-3.93 (br s, 1H).

Anal. Calcd for C$_{23}$H$_{41}$N$_3$O$_8$: C, 56.66; H, 8.48; N, 8.62; O, 26.25.

Found: C, 56.48; H, 8.46; N, 8.39.

12) tert-Butyl (3S,5R)-3-[(2-methylpropyl)amino]-5-(morpholin-4-ylcarbonyl)piperidine-1-carboxylate succinate (30.3 g, 62.2 mmol), acetonitrile (60.0 mL) and water (40.0 mL) were charged. Then, potassium carbonate (34.4 g, 0.249 mmol) was added, and the mixture was stirred for 10 min. 1-(4-Methoxybutyl)-2-trichloromethyl-1H-benzimidazole (20.0 g, 62.2 mmol) was added, and the mixture was stirred at 70-80° C. for 2 hr. Dimethyl sulfoxide (15.0 mL) was added, and the mixture was stirred at 70-80° C. for 6 hr. The reaction mixture was allowed to cool to 20-30° C. water (120 mL) and toluene (240 mL) were added, and the mixture was partitioned. The organic layer was washed successively with 10 w/v % brine (100 mL), 10 w/v % aqueous citric acid solution (100 mL) and 10 w/v % brine (100 mL). To the organic layer was added activated carbon Shirasagi A (1.0 g), and the mixture was stirred at 20-30° C. for 30 min. The activated carbon was filtered off and washed with toluene (40.0 mL), and the filtrate was concentrated under reduced pressure to 110 mL. After heating to 35-45° C., heptane (280 mL) was added dropwise tert-Butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate as crystals (10 mg) was added at 35-45° C., and the mixture was stirred at the same temperature for 1 hr. Heptane (140 mL) was added dropwise at 35-45° C., and the mixture was stirred for 30 min. The mixture was allowed to cool to 20-30° C. and stirred for 2 hr. The precipitated crystals were collected by filtration, washed with toluene-heptane (1:5, 40.0 mL), and dried under reduced pressure at 50° C. to give tert-butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate as a pale yellowish white crystalline powder (27.7 g, yield 74.2%).

$^1$H-NMR (300 MHz, CDCl$_3$) δ 0.68-0.80 (m, 3H), 0.96-1.08 (m, 3H), 1.31 (br s, 5H), 1.49 (s, 4H), 1.61-1.71 (m, 2H), 1.71 (br s, 0.5H), 1.92-2.05 (m, 3H), 2.05-2.24 (m, 2H), 2.45 (br s, 1H), 2.60 (br s, 1H), 2.72-2.96 (m, 2H), 3.26-3.35 (m, 3H), 3.35-3.47 (m, 2H), 3.47-3.73 (m, 10H), 4.02-4.26 (m, 2H), 4.26-4.34 (m, 1H), 4.34-4.47 (m, 0.5H), 7.25-7.29 (m, 1H), 7.29-7.41 (m, 1H), 7.41-7.53 (m, 1H), 7.64 (br s, 0.5H), 7.79 (d, J=8.2 Hz, 0.5H).

Anal. Calcd for C$_{32}$H$_{49}$N$_5$O$_6$: C, 64.08; H, 8.23; N, 11.68; O, 16.01.

Found: C, 63.82; H, 8.12; N, 11.64.

Example 1

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal)

tert-Butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate (20 kg) was added to aqueous 3N hydrochloric acid (concentrated hydrochloric acid 20 L, water 60 L) prepared in advance, and then ethyl acetate (4 L) was added. After the addition, the mixture was stirred at 15-25° C. for 3 hr or longer. After completion of the reaction, water (100 L) and ethyl acetate (200 L) were added at the same temperature. After the addition, the mixture was adjusted with 25% aqueous ammonia (about 19 L) to around pH 7 at 25° C. or lower. After pH adjustment, the extracted organic layer was preserved and the aqueous layer was extracted again with ethyl acetate (200 L). The re-extracted organic layer was preserved and the aqueous layer was extracted again with ethyl acetate (200 L). The same operation was repeated again, and the obtained organic layers were combined and the mixture was concentrated. After concentration, ethyl acetate (100 L) was added and the mixture was concentrated again. The same operation was repeated again. After concentration, ethyl acetate (125 L) and 2-propanol (20 L) were added, and the mixture was heated to 35-45° C. After temperature rise, 4N hydrogen chloride-ethyl acetate (8.34 L) was added at the same temperature. After the addition, the seed crystals (20 g) of type B crystal obtained according to the method described in Example (6-3) was added at the same temperature, and the mixture was stirred for 30 min or longer. After stirring, heptane (200 L) was added dropwise at 35-45° C. over 30 min or longer. After completion of the dropwise addition, the mixture was stirred at the same temperature for 30 min or longer. Then, the mixture was slowly cooled to 20-30° C. and stirred at the same temperature for 30 min or longer. After stirring, the crystals were collected by filtration and washed with 2-propanol-ethyl acetate-heptane (1:6:8, 60 L) to give wet crystals. The obtained wet crystals were dried under reduced pressure at 45-55° C. to give 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a crystalline powder (type B crystal, 16.446 kg, yield 92.0%).

Example 2

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal)

1-(4-Methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal, 16.3 kg) was suspended in 2-propanol (65.2 L). Then, the suspension was dissolved by heating to 65-75° C. After confirmation of the dissolution, dust removal filtration was carried out, and the residue was washed with 2-propanol (16.3 L). The obtained filtrate and washing was cooled to 50-60° C., and the seed crystals (16.3 g) of type B crystal obtained according to the method described in Example (6-3) was added. After addition, the mixture was allowed to cool to 45-55° C., and the mixture was stirred at the same temperature for 30 min or longer. After stirring, heptane (326 L) was added dropwise at the same temperature over 30 min or longer. After completion of the dropwise addition, the mixture was stirred at the same temperature for 1 hr or longer. After stirring, the mixture was allowed to cool to 20-30° C. and stirred at the same temperature for 1 hr or longer. After stirring, the crystals were collected by filtration and washed with 2-propanol-heptane (1:4, 48.9 L) to give wet crystals. The obtained wet crystals were dried under reduced pressure at 45-55° C. to give a crystalline powder (type B crystal, 13.28 kg, yield 81.5%). melting point: 198° C.

As a result of a hydrochloric acid content analysis, the above-mentioned hydrochloride was confirmed to be monohydrochloride.

theoretical hydrochloric acid content 6.8%, measured value 6.9%

Example 3

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal)

The type A crystal (3.0 g) obtained according to the method described in Reference Example 1 was suspended in 2-propanol (30 mL) at room temperature, and the suspension was dissolved at 30-40° C. After confirmation of the dissolution, the seed crystals (0.003 g) of type B crystal obtained according to the method described in Example 4 was added. After addition, the mixture was allowed to cool to 20-30° C. and stirred overnight. After stirring, the crystals were collected by filtration and washed with 2-propanol (9 mL) to give wet crystals. The obtained wet crystals were dried under reduced pressure at 50° C. to give a crystalline powder (type B crystal, 2.03 g, yield 67.7%).

Example 4

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal)

The type A crystal (550 g) obtained according to the method described in Reference Example 2 was suspended in methyl ethyl ketone (4400 mL), and the suspension was heated to 45-55° C. After stirring, methyl ethyl ketone (1000 mL) was added. After addition, the mixture was stirred while rising the temperature to 50-60° C., allowed to cool to 20-30° C. and stirred. After stirring, the crystals were collected by filtration and washed with methyl ethyl ketone (80 mL) to give wet crystals. The obtained wet crystals were dried under reduced pressure at 45-50° C. to give a crystalline powder (type B crystal, 531.95 g, yield 96.7%).

Example 5

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal)

The type A crystal (6.0 g) obtained according to the method described in Reference Example 2 was suspended in 2-propanol-ethyl acetate (1:15, 54 mL) at room temperature, and the suspension was stirred while heating to 45-55° C. Precipitation of crystals was observed as the dissolution proceeded. After observation of crystal precipitation, the mixture was allowed to cool to 20-30° C., and stirred overnight. After stirring, the crystals were collected by filtration and washed with ethyl acetate (18 mL) to give wet crystals. The obtained wet crystals were dried under reduced pressure at 50° C. to give a crystalline powder (type B crystal, 5.72 g, yield 95.3%).

Example 6

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal)

(6-1)

1-(4-Methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal, 45.0 g) was suspended in 2-propanol (360 mL). Then, the suspension was dissolved by heating to 55-60° C. After confirmation of the dissolution, dust removal filtration was carried out, and the residue was washed with 2-propanol (45 mL). The filtrate and washing after the dust removal filtration were stirred at 55-65° C., but no precipitation was confirmed. After confirmation, the solution was allowed to cool to 35-45° C. After cooling, the seed crystals (0.045 g) of type B crystal obtained according to the method described in Example 3 was added. After addition, the mixture was stirred at the same temperature for 1 hr or longer. After stirring, heptane (1620 mL) was added dropwise at the same temperature. After dropwise addition, the mixture was stirred at the same temperature for 30 min or longer. After stirring, the mixture was allowed to cool to 20-30° C. and stirred for 1 hr or longer. After stirring, the crystals were collected by filtration and washed with 2-propanol-heptane (1:4, 135 mL) to give wet crystals. The obtained wet crystals were dried under reduced pressure at 50° C. to give 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a crystalline powder (type B crystal, 40.37 g, yield 89.7%).

(6-2)

1-(4-Methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal, 500 g) was suspended in 2-propanol (4000 mL). Then, the suspension was dissolved by heating to 55-65° C. After confirmation of the dissolution, dust removal filtration was carried out, and the residue was washed with 2-propanol (250 mL). Similarly, 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal, 500 g) was suspended in 2-propanol (4000 mL). Then, the suspension was dissolved by heating to 55-65° C. After confirmation of the dissolution, dust removal filtration was carried out, and the residue was washed with 2-propanol (250 mL). The two filtrates and washings after the above-mentioned dust removal filtration were combined and stirred at 55-65° C., but no precipitation was confirmed. The used containers were washed with 2-propanol (500 mL). After confirmation, the solution was allowed to cool to 35-45° C. After cooling, the seed crystals (1 g) of type B crystal obtained according to the method described in Example (6-1) was added, and heptane (36000 mL) was added dropwise at the same temperature. After dropwise addition, the mixture was stirred at the same temperature for 1 hr or longer. After stirring, the mixture was allowed to cool to 20-30° C. and stirred for 1 hr or longer.

After stirring, the crystals were collected by filtration and washed with 2-propanol-heptane (1:4, 3000 mL) to give wet crystals. The obtained wet crystals were dried under reduced pressure at 50° C. to give 1-(4-methoxybutyl)-N-(2-methyl-propyl)-N-[(3S,5R)-5-(morpholin-4-ylcarbonyl)piperidin-3-yl]-1H-benzimidazole-2-carboxamide hydrochloride as a crystalline powder (type B crystal, 880.53 g, yield 88.1%). The obtained type B crystal was pulverized in a Power Mill to give a crystalline powder (pulverized product, type B crystal, 849 g).

(6-3)

1-(4-Methoxybutyl)-N-(2-methylpropyl)-N-[(3S,5R)-5-(morpholin-4-ylcarbonyl)piperidin-3-yl]-1H-benzimidazole-2-carboxamide methanesulfonate monohydrate (9000 g) was dissolved in water (45000 mL). Sodium bicarbonate water (NaHCO$_3$ 2464 g, water 45000 mL) prepared in advance was added to the dissolved solution and the mixture was stirred. With stirring, ethyl acetate (90000 mL) was added and the mixture was stirred. After stirring, ethyl acetate (90000 mL) was added to the extracted aqueous layer and the mixture was stirred. After stirring, ethyl acetate (90000 mL) was added to the extracted aqueous layer again and the mixture was stirred. The obtained organic layers were combined and concentrated to about 27 L. To the concentrated solution was added ethyl acetate (45000 mL), and the mixture was concentrated to about 27 L. The concentrated solution was left standing overnight. To the concentrated solution left standing overnight was added ethyl acetate (45000 mL), and the mixture was concentrated to about 27 L. To the concentrated solution were added ethyl acetate (45000 mL) and 2-propanol (9000 mL), and the mixture was heated to 45-55° C. with stirring. While heating, 4N hydrogen chloride-ethyl acetate (4399 mL) was added dropwise at 40° C. After dropwise addition, the solution was confirmed to be homogeneous and allowed to cool to 35-45° C. After cooling, the seed crystals (9 g) of type B crystal obtained according to the method described in Example (6-2) was added, and heptane (90000 mL) was added dropwise at the same temperature. After completion of the dropwise addition, the mixture was stirred at the same temperature for 1 hr or longer. After stirring, the mixture was cooled to 20-30° C. and stirred at the same temperature for 1 hr or longer. The crystals were collected by filtration and washed with 2-propanol-ethyl acetate-heptane (1:6:8, 9000 mL) to give wet crystals. The obtained wet crystals were dried under reduced pressure at 50° C. to give 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a crystalline powder (type B crystal, 7271 g, yield 92.5%). The obtained 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride (type B crystal, 3500 g) was suspended in 2-propanol (28000 mL). Then, the suspension was dissolved by heating to 55-65° C. After confirmation of the dissolution, dust removal filtration was carried out, and the residue was washed with 2-propanol (3500 mL). The filtrate and washing after the dust removal filtration were stirred at 55-65° C. but no precipitation was confirmed. After confirmation, the solution was allowed to cool to 35-45° C. After cooling, the seed crystals (3.5 g) of type B crystal obtained according to the method described in Example (6-2) was added, and heptane (126000 mL) was added dropwise at the same temperature. After dropwise addition, the mixture was stirred at the same temperature for 1 hr or longer. After stirring, the mixture was allowed to cool to 20-30° C. and stirred for 1 hr or longer. After stirring, the crystals were collected by filtration and washed with 2-propanol-heptane (1:4, 10500 mL) to give wet crystals. The obtained wet crystals were dried under reduced pressure at 50° C. to give 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride as a crystalline powder (type B crystal, 3089 g, yield 88.3%). The obtained type B crystal (3074 g) was pulverized in a Power Mill to give a crystalline powder having a powder X-ray diffraction pattern showing characteristic peaks at interplanar spacings (d) of around 26.43, 7.62, 4.32, 3.08, 2.59 and 2.33 angstroms (pulverized product, type B crystal, 3066 g, yield 99.7%). The measurement results of powder X-ray diffraction are shown in the following Table.

TABLE 2

Powder X-ray diffraction data (type B crystal)

| 2θ (°) | d value (Å) | relative intensity (%) |
|---|---|---|
| 3.34 | 26.43 | 100 |
| 11.60 | 7.62 | 12 |
| 20.54 | 4.32 | 29 |
| 28.98 | 3.08 | 15 |
| 34.54 | 2.59 | 14 |
| 38.64 | 2.33 | 11 |

Experimental Example 1

Slurry Interconversion

Type A crystal, type B crystal, and a mixture (1:1) of type A crystal and type B crystal (each 20 mg) were measured in vials, and isopropyl alcohol (0.2 mL) was added to give suspension containing excess solids remaining therein. The vial was sealed, and shaken on a slurry wheel at ambient temperature for 1 day at steady rotation. Thereafter, the solids were collected by filtration. As a result of powder X-ray diffraction measurements, type A crystal, and the mixture (1:1) of type A crystal and type B crystal were confirmed to convert to type B crystal in one day. Type B crystal showed no change. The results are shown in Table 3.

From the results of slurry experiment, type B crystal was assumed to be thermodynamically stable at ambient temperature as compared to type A crystal.

TABLE 3

Results of slurry experiment at ambient temperature

| solvent | compound amount (mg) | solvent volume (mL) | crystal form before slurry | 1 day later |
|---|---|---|---|---|
| isopropyl alcohol | 20 | 0.2 | type A crystal | type B crystal |
| isopropyl alcohol | 20 | 0.2 | type B crystal | type B crystal |
| isopropyl alcohol | 20 | 0.2 | mixture (1:1) of type A crystal and type B crystal | type B crystal |

Experimental Example 2

Moisture Adsorption Analysis

Moisture adsorption of type A crystal and type B crystal was automatically analyzed by VTI Symmetrical Gravimetric Analyzer in step-isothermal mode (SGA-100 for type A crystal, SGA-CX for type B crystal). Samples were exposed various relative humidities (RH) at 25° C. The weight of the samples at each relative humidity was recorded after equilibrium (weight change of less than 0.02% within 10 min). The results are shown in Table 4.

TABLE 4

| type A crystal | | type B crystal | |
|---|---|---|---|
| relative humidity (% RH) | level (%) of weight change | relative humidity (% RH) | level (%) of weight change |
| 30 | −0.1 | 30 | 0.0 |
| 50 | 0.0 | 50 | 0.5 |
| 70 | 7.6 | 70 | 0.9 |

Experimental Example 3

Dissolution Test

To type A crystal and type B crystal (each 50 mg) were added 2-butanone, ethyl acetate, toluene, n-heptane and tert-butylmethylether (each 5 mL), and the dissolution property was measured using a powder suspension (25° C., 2 hr). The suspension was centrifuged, the supernatant was filtered with a filter (pore size 0.22 μm), and the solvent was evaporated from the filtrate under a nitrogen atmosphere. The residue obtained by evaporation was dissolved in a mixed solution of 50 mM aqueous ammonium acetate solution/acetonitrile (1:1), and measured by HPLC. The results are shown in Table 5.

From these results, type B crystal was assumed to be thermodynamically stable at room temperature (25° C.) as compared to type A crystal.

TABLE 5

| | solubility (μg/mL) | |
|---|---|---|
| | type A crystal | type B crystal |
| 2-butanone | >10000 | 1800 |
| ethyl acetate | 7300 | 280 |
| toluene | >10000 | 4.6 |
| n-heptane | 1.7 | 0.8 |
| tert-butyl methyl ether | 49 | 13 |

INDUSTRIAL APPLICABILITY

The crystal of the present invention has a superior rennin inhibitory activity, and is useful for the prophylaxis or treatment of hypertension and various organ disorders caused by hypertension, and the like.

This application is based on patent application No. 2010-137194 filed in Japan, the contents of which are encompassed in full herein.

The invention claimed is:

1. A crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride having a powder X-ray diffraction pattern showing characteristic peaks at interplanar spacings (d) of 26.43±0.2, 7.62±0.2 and 4.32±0.2 angstroms.

2. A crystal of 1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride having a powder X-ray diffraction pattern showing characteristic peaks at interplanar spacings (d) of 26.43±0.2, 7.62±0.2, 4.32±0.2, 3.08±0.2, 2.59±0.2 and 2.33±0.2 angstroms.

3. A medicament comprising the crystal of claim 1 or 2.

4. The medicament of claim 3, which is a rennin inhibitor.

5. The medicament of claim 3, which is a therapeutic agent for hypertension.

6. A method for the treatment of hypertension in a mammal, comprising administering an effective amount of the crystal of claim 1 or 2 to said mammal.

7. The crystal of claim 1 or 2 for use in the treatment of hypertension.

* * * * *